United States Patent [19]

Endo et al.

[11] Patent Number: 4,725,148

[45] Date of Patent: Feb. 16, 1988

[54] TURBIDIMETER EMPLOYING A SEMICONDUCTOR LASER DIODE AND A PHOTODIODE

[75] Inventors: Isao Endo, Kokubunji; Teruyuki Nagamune, Kamifukuoka; Ichiro Inoue, Tokyo; Kozo Inoue, Ichikawa; Tadashi Nohira, Shiroi; Ikuzo Kagami, Tokyo; Tatsuya Iwakura, Yokohama, all of Japan

[73] Assignees: Komatsugawa Chemical Engineering Co., Ltd., Tokyo; Rikagaku Kenkyusho, Wako; Fuji Facom Corporation, Hino, all of Japan

[21] Appl. No.: 739,319

[22] Filed: May 30, 1985

[30] Foreign Application Priority Data

Jun. 7, 1984 [JP] Japan ............................. 59-115409

[51] Int. Cl.⁴ ...................... G01N 21/59; G01N 21/84
[52] U.S. Cl. .............................. 356/442; 250/205; 250/573; 435/291
[58] Field of Search ............................. 356/440–442; 250/205, 564–565, 573–574, 576, 552; 435/3, 289, 291; 374/17

[56] References Cited

U.S. PATENT DOCUMENTS

| | | | |
|---|---|---|---|
| 3,188,857 | 6/1965 | Vesper et al. | 374/17 X |
| 3,551,670 | 9/1970 | Topol et al. | 356/442 X |
| 3,705,316 | 12/1972 | Burrous et al. | 250/205 X |
| 3,734,629 | 5/1973 | Griffiths | 356/441 X |
| 3,819,278 | 6/1974 | Muller | 356/442 |
| 3,838,926 | 10/1974 | Kato et al. | 356/442 |
| 3,892,485 | 7/1915 | Merritt et al. | 356/442 X |
| 3,973,852 | 8/1976 | Moore et al. | 250/552 X |
| 4,056,719 | 11/1977 | Waaben | 250/205 X |
| 4,561,779 | 12/1985 | Nagamune et al. | 356/440 X |

FOREIGN PATENT DOCUMENTS

56-49551 11/1981 Japan.
57-201954 12/1982 Japan.

OTHER PUBLICATIONS

Marchand et al, "A High-Precision & Large-Capacity Laser Biophotometer", Applied Microbiology, May 1974, pp. 874–877.

Mackintosh et al, "Development and Further Applications of a Simple Turbidity Cell for Continuously Monitoring Bacterial Growth", Phys. Med. Biol., vol. 18, No. 2, pp. 265–271, Mar. 1973.

*Primary Examiner*—Vincent P. McGraw
*Attorney, Agent, or Firm*—Spencer & Frank

[57] ABSTRACT

In a turbidimeter for measuring a turbidity of a test solution to be measured i.e. culture solution in a fermentation apparatus, a semiconductor laser diode and a semiconductor photodiode are integrally arranged in a detection portion of the turbidimeter in such a manner that a laser beam emitted from the semiconductor laser diode is made incident upon the semiconductor photodiode through the test solution. Moreover, a protection circuit for the semiconductor laser diode and the semiconductor photodiode is also arranged in the turbidimeter to cut off a current flowed therethrough when an environmental temperature becomes above a predetermined temperature. Therefore, the turbidimeter can be made small in size and light in weight, and the turbidity can be measured accurately over wide range.

29 Claims, 8 Drawing Figures

FIG_6

TURBIDIMETER EMPLOYING A SEMICONDUCTOR LASER DIODE AND A PHOTODIODE

BACKGROUND OF THE INVENTION

The present invention relates to a turbidimeter which is preferably used for measuring the turbidity of a culture solution or suspension in a fermentation apparatus.

When measuring the turbidity of culture solutions in industrial apparatuses, a tungsten lamp is widely used as the light source. However, the tungsten lamp has many drawbacks such that its light intensity varies greatly, its life cycle is short, its temperature becomes high and the color of test solutions is greatly affected. In order to eliminate the drawbacks mentioned above, there has been proposed in, for example, Japanese Patent Publication No. 49,551/81 a turbidimeter using a light-emitting diode as the light source. However, since it is not possible to measure the turbidity above 10% due to the weak light emitted from the light-emitting diode and the measurement is largely affected by temperature, it is necessary to measure the test solution or a diluted test solution by introducing it into a flowcell manually or through a bypass pipe without directly immersing the turbidimeter in the test solution in the apparatus. Therefore, there occurs a drawback such that the apparatus is liable to be large in size and complicated in construction. Especially in the case of measuring a diluted test solution, the measuring accuracy is largely affected by errors due to the dilution.

Further, there is disclosed in "Applied Microbiology," vol 27, No. 5, May 1974, pages 874–877 and Japanese Utility Model Laid-Open Publication No. 201,954/83 a turbidimeter utilizing a He-Ne gas laser as the light source and a photomultiplier tube as a light-receiving device. in In the turbidimeter mentioned above, since the He-Ne gas laser emits strong laser light, there is the possibility of measuring a test solution having relatively large turbidity without diluting it. However, since the He-Ne gas laser device and the apparatus including the photomultiplier tube are liable to be large in size, it is very difficult to install them integrally with the industrial apparatus together with a detection device. Therefore, it is necessary to arrange the He-Ne gas laser device and the apparatus including the photomultiplier tube separately from the industrial apparatus containing the test solution i.e. a suspension to be measured therein and to connect therebetween by means of optical fibers, so that the strong laser light cannot be utilized effectively due to a loss of laser light transmitting through the optical fibers or connectors of the optical fibers. Moreover, the apparatus becomes large in size and inspection and maintenance thereof become very troublesome.

SUMMARY OF THE INVENTION

The present invention has for its object to eliminate the drawbacks mentioned above and to provide a turbidimeter which can accurately measure turbidity over a wide range without being affected by temperature and which can be directly installed in an industrial apparatus including a test solution to be measured. Here, the term "directly installed in an industrial apparatus" means that the turbidimeter according to the invention is directly arranged in a fermentation tank or a pipe in which a fermented solution (suspension) flows, and thus the turbidity of the test solution i.e. the fermented solution can be directly measured without sampling it.

According to the invention, a turbidimeter for measuring the turbidity of a test solution to be measured, comprises:
  a detection portion connected directly to a device containing said test solution therein; and
  a semiconductor laser diode and a semiconductor photodiode, both diodes being integrally secured to said detection portion in such a manner that a laser beam emitted from said semiconductor laser diode is made incident upon said semiconductor photodiode through said test solution.

The present inventors have performed various experiments and succeeded in the development of a turbidimeter which can be directly installed in an industrial apparatus containing the test solution to be measured by utilizing a semiconductor laser diode as the light source and a semiconductor photodiode as the light-receiving device. The light output of the semiconductor laser diode is very strong and stable over a very long lift cycle. Moreover, it is not affected by the color of the test solution to be measured. Therefore, the turbidity of a suspension having high turbidity and dark color can be accurately measured.

The turbidimeter according to the invention can be used in various fields, and especially it is preferable to use the turbidimeter for measuring a culture solution in the fermentation device. In this case, since the correlation between the measured turbidity and a bacterial cell mass concentration is high, it is possible to measure directly the bacterial cell mass concentration over a wide range without diluting the culture solution. Moreover, in such fermentation devices, sterilization is performed under high temperature, but it is not necessary to remove the turbidimeter from the fermentation device every time the sterilization is effected under high temperature. That is to say, the maximum permitted temperatures of the semiconductor laser diode and the semiconductor photodiode are normally low in the range 60°~70° C. when a current is flowing therethrough, but the temperature of the culture solution is normally under 50° C. when the turbidity of the culture solution is measured by the current flowing through these diodes, so that no difficulty results. Moreover, when effecting sterilization under high temperature, the temperature of the fermentation tank becomes high such as 120°~125° C., but the maximum permitted temperatures of the semi-conductor laser diode and the semiconductor photodiode are also high such as 60°~125° C. when no current is flowing therethrough, so that there occurs no trouble if use is made of a diode having the maximum permitted temperature of 125° C. when no current flows therethrough. Further, as shown in the embodiments to be explained hereinafter, the temperature around these diodes can be maintained below the maximum permitted temperature by providing a heat insulating material and a protection circuit for inhibiting forcedly the current flowing through the semiconductor photodiode when sterilization is performed under high temperature, so that breakage of these diodes can be completely avoided.

DESCRIPTION OF THE PREFERRED EMBODIMENTS

Figure 1:
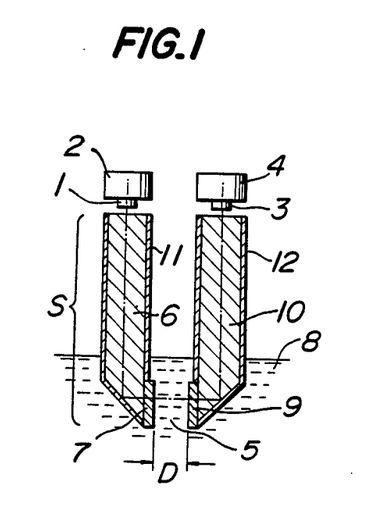
FIG. 1 is a cross sectional view showing the construction of a main portion of the turbidimeter according to the invention.

FIG. 1 is a cross sectional view showing the construction of a main portion of the turbidimeter according to the invention. In the turbidimeter according to the invention, a light-emitting portion 2 including a semiconductor laser diode 1 and a light-receiving portion 4 comprising a semiconductor photodiode 3 are arranged integrally with a detection portion S. The dectection portion S comprises a first combination of a prism 6 and a light scattering plate 7 for introducing a laser beam emitted from the semiconductor laser diode 1 to a gap 5 arranged at the lowermost portion thereof and a second combination of a light scattering plate 9 and a prism 10 for introducing a laser beam transmitted through a test solution 8 in the gap 5 to the semiconductor photodiode 3. The light scattering plates 7 and 9 can be made of an opaque or translucent quartz (crystal including bubbles) or an opal glass, and the prisms 6 and 10 can be made of a material such as quartz, pyrex glass and crystal. Further, sides of the prisms 6 and 10 other than light exit and inlet portions may be covered with reflection mirrors 11 and 12 provided by aluminum evaporation. Moreover, the distance D of the gap 5 may be selected suitably corresponding to the test solution to be measured, and when the fermented culture solution is to be measured it can be set to 1 mm~2 mm.

The high intensity laser beam emitted from the semiconductor laser diode 1 in the light emitting portion 2 is transmitted through the prism 6 and is scattered by the light scattering plate 7. Further, the scattered laser beam is made incident upon the test solution 8 existent in the gap 5 and is scattered by particles in th test solution 8. Therefore, the amount of light transmitted through the test solution 8 is in inverse proportion to the turbidity of the test solution 8. That is to say, the amount of light transmitted through the test solution 8 decreases when the turbidity of the test solution 8 is high and increases when the turbidity is low. Further, the transmitted light beam is made incident upon the semiconductor photodiode 3 through the light scattering plate 9 and the prism 10. Then, the turbidity of the test solution 8 can be measured by suitably processing an output of the semiconductor photodiode 3.

Figure 2:
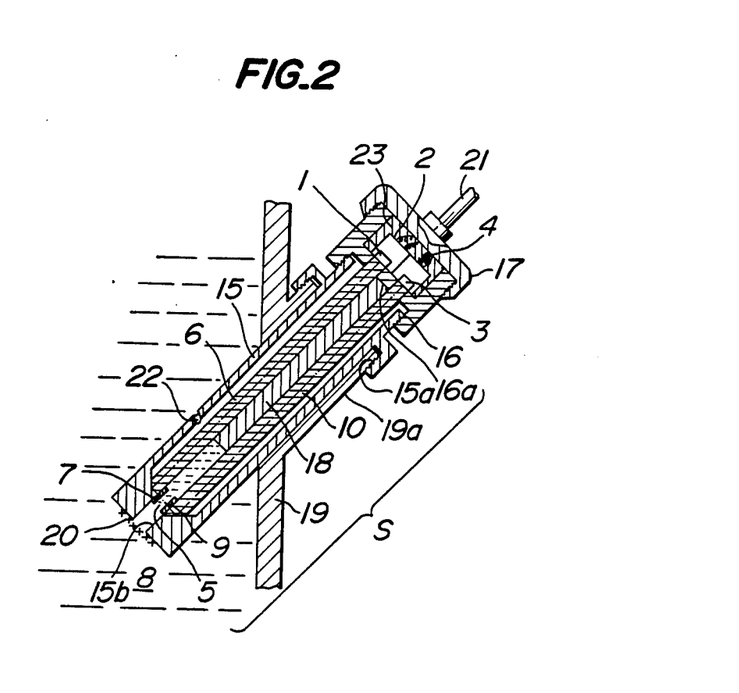
FIG. 2 is a cross sectional view illustrating one embodiment of the turbidimeter according to the invention.

FIG. 2 is a cross sectional view showing one embodiment of the invention in which the turbidimeter is provided in a wall of a fermentation apparatus. In this embodiment, the optical system from the semiconductor laser diode to the semiconductor photodiode is essenially the same as those shown in FIG. 1, and portions in FIG. 2 similar to those shown in FIG. 1 are denoted by the same reference numerals used in FIG. 1. In FIG. 2 the housing of the detection portion S is constructed of a cylindrical member 15, supporting member 16 and cap member 17, and these members are screwed together. The light-emitting portion 2 including the semiconductor laser diode 1 and the light-receiving portion 4 including the semiconductor photodiode 3 are arranged on a circular portion 16a of the supporting member 16. The prisms 6 and 10 are supported by the circular portion 16a through holes formed in the circular portion 16a. An opaque spacer 18 is arranged between prisms 6 and 10. At the upper portion of the cylindrical member 15 a thread portion 15a having a diameter larger than that of the cylindrical member 15 of formed, and is engaged with a thread formed in a cylinder 19a formed integrally with a wall 19 of an industrial apparatus. As a result, the turbidimeter is fixed to the wall 19 of the apparatus containing the test solution 8. In this case, it is necessary to immerse the lower end of the cylindrical member 15 into the test solution 8. At the lower end of the cylindrical member 15 is formed a hole 15b which is covered with a net 20 made of metal. The net 20 functions to prevent fine bubbles from being introduced into the turbidimeter. Moreover, an opening 22 for discharging the test solution functions to circulate the tests solution 8 through the gap 5. Further, a tube 21 is connected to the cap member 17 through a connector so as to connect the light-emitting portion 2 and the light-receiving portion 4 to external circuits.

As shown in FIG. 2, if the turbidimeter is secured to the wall 19 of an apparatus such as a fermentation apparatus in which the test solution 8 is existent, the semiconductor laser diode 1 and the semiconductor photodiode 3 can be arranged outside the fermentation apparatus, and the prisms 6 and 10 having low thermal conductivity can be arranged between the test solution 8, i.e. The culture solution and the semiconductor laser diode 1 and photodiode 3. As a result, it is possible to minimize the thermal influence upon the semiconductor laser diode 1 and the semiconductor photodiode 3. that is to say, the prisms 6 and 10 can also serve as a heat insulating material. Moreover, the space in the housing surrounding the laser diode 1 and the photodiode 3 is filled with a heat insulating material 23 so as to prevent heat conduction to these diodes. In the fermentation apparatus, when the normal fermentation is effected, the temperature of the test solution 8 is about 20°~50° C. At that temperature, the semiconductor laser diode 1 and the semiconductor photodiode 3 are not damaged even if current is flowing therethrough. Morevoer, when sterilization of the fermentation apparatus is effected under high temperature, use is made of steam having a temperature of 120°~125° C. for a long time. However, especially in the present embodiment, since the semiconductor laser diode 1 and the semiconductor photodiode 3 are arranged outside the apparatus and insulated from heat by the prisms 6, 10 and the heat insulating material 23, the temperature of the semiconductor laser diode 1 and the semiconductor photodiode 3 does not increase up to the maximum permitted temperature thereof even if current is flowing therethrough. Moreover, during sterilization under high temperature, the current flowing through the semiconductor laser diode 1 and the semiconductor photodiode 3 is stopped, so that these diodes 1 and 3 are not damaged at all even if the turbidimeter is not removed from the fermentation apparatus. This is very advantageous for automatic control of the fermentation process and elimination of labor.

In the present embodiment, the apparatus is made forcedly inoperative by means of a driving circuit to be described below when the temperature of the measuring region is above the predetermined temperature.

Figure 3:
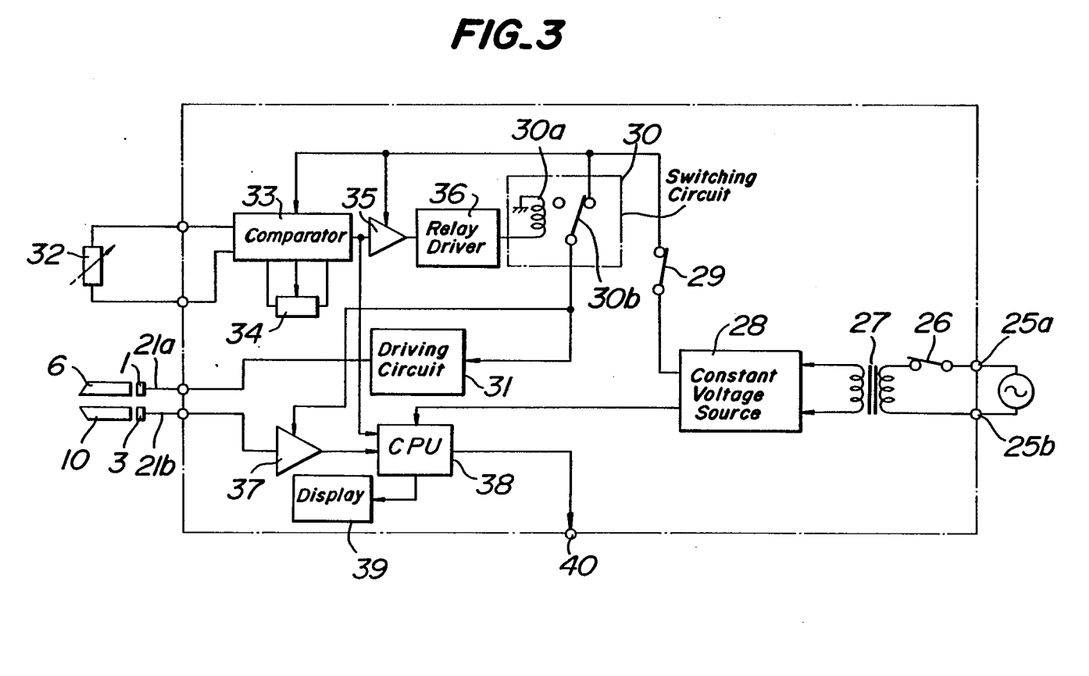
FIG. 3 is a circuit diagram depicting one embodiment of a driving circuit of a semiconductor laser diode.

FIG. 3 is a circuit diagram showing one embodiment of the driving circuit including a temperature protection circuit. Commercially available AC power applied to power input terminals 25a and 25b is supplied to a DC constant voltage source 28 through a power switch 26 and a transformer 27. A DC voltage supplied from the constant voltage source 28 is applied to a driving circuit 31 through an on and off switch 29 for the semiconductor laser diode 1 and the semiconductor photodiode 3 and through a switching circuit 30. Moreover, a driving signal from the driving circuit 31 is supplied to the semiconductor laser diode 1 through a lead wire 21a. The switching circuit 30 comprises a relay coil 30a and a relay contact 30b and is normally maintained at the state shown in FIG. 3. In this embodiment, when the relay coil 30a is energized, the relay contact 30b is switched so that the driving circuit 31 is disconnected from the constant voltage source 28.

In this embodiment, the relay coil 30a is controlled by the temperature of the measuring region in such a manner that the relay coil 30a is energized so as to make inoperative the semiconductor laser diode 1 when the temperature rises above the predetermined temperature. To this end, use is made of a thermistor 32 for detecting the temperature of the measuring region, and the thermistor 32 is connected to a comparator 33. The thermistor 32 is arranged near the semiconductor laser diode 1. Further, the potentiometer 34 for setting the cutoff temperature is connected to the comparator 33. Therefore, an output signal is generated from the comparator 33 when the temperature detected by the thermistor 32 rises above the predetermined temperature. This output signal is amplified by an amplifier 35, and then the amplified signal is supplied to a relay coil driving circuit 36. When the relay coil driving circuit 36 receives this amplified signal, the relay coil 30a is energized, so that the relay contact 30b is driven into the position opposite to that shown in FIG. 3. Then, the voltage is not applied to the driving circuit 31, and thus the semiconductor laser diode 1 is maintained inoperative. In this manner, the semiconductor laser diode 1 can be advantageously protected from breakage.

An output signal supplied from the semiconductor photodiode 3 is supplied to a central processing unit (CPU) 38 through a lead wire 21b and an amplifier 37 so as to generate a signal representing turbidity by suitably processing the supplied signal therein. This signal can be supplied to an indicator 39 to display the measured turbidity and further supplied to an external apparatus such as a memory unit through an output terminal 40. Moreover, an output signal of the comparator 33 representing whether the semiconductor laser diode 1 is active or inactive is also supplied to the central processing unit 38 so as to display the state of the semiconductor laser diode 1. In this case, since the voltage is applied to the amplifier 37 through the switching circuit 30, the semiconductor photodiode 3 becomes inactive when the relay contact 30b is opened by an increase of temperature.

As mentioned above, breakage of the semiconductor laser diode and the semiconductor photodiode due to temperature increase can be advantageously avoided, but since the light output emitted from the semiconductor laser diode varies in response to temperature changes and the operational characteristics of the semiconductor photodiode also depends upon the temperature, it is preferable to arrange a temperature compensation means for these diodes.

Figure 4:
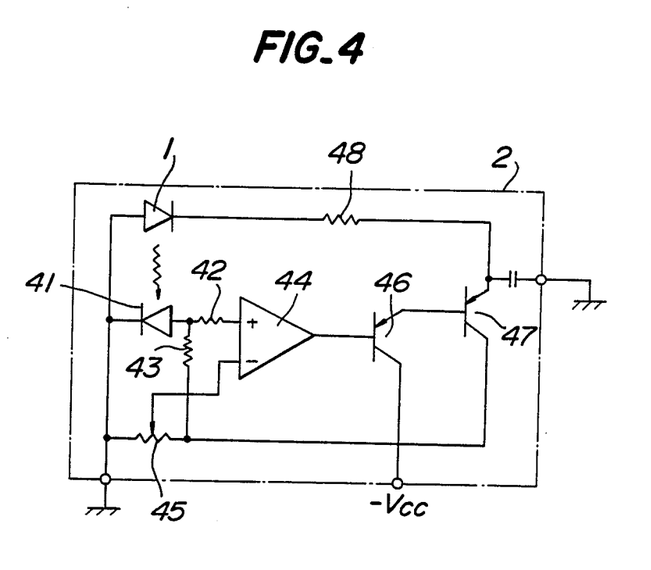
FIG. 4 is a circuit diagram showing one embodiment of a light-emitting portion having a temperature compensation circuit.

FIG. 4 is a circuit diagram showing one embodiment of the light-emitting portion in which means for keeping the light output of the semiconductor laser diode constant even if the temperature is varied is installed. In the light-emitting portion 2, a semiconductor photodiode 41 is arranged to receive directly a part of the laser beam emitted from the semiconductor laser diode 1. The anode of the semiconductor photodiode 41 is connected to a positive input terminal of a differential amplifier 44 through resistors 42 and 43 for dividing the voltage. A negative input terminal of the differential amplifier 44 is connected to a slide tap of a potentiometer 45. An output terminal of the differential amplifier 44 is connected to transistors 46 and 47 which comprise a Darlington amplifier. The emitter of the transistor 47 is connected to the cathode of the semiconductor laser diode 1 through a resistor 48. The anode of the semiconductor laser diode 1 and the cathode of the photodiode 41 are commonly connected to ground.

In this embodiment, if the environmental temperature is increased and the output of the laser beam is decreased, the amount of light incident upon the semiconductor photodiode 41 is also decreased. As a result, the potential of the positive input terminal of the differential amplifier 44 is decreased, and the output voltage of the differential amplifier 44 is decreased correspondingly. Therefore, the transistors 46 and 47 become more conductive, and a larger current flows through the semiconductor laser diode 1, so that the laser beam emitted from the semiconductor laser diode 1 becomes stronger. In this manner, the laser beam intensity emitted from the semiconductor laser diode 1 can be maintained constant even if the environmental temperature is varied.

In this embodiment, the output of the laser beam is maintained constant against temperature variations, but it is possible to keep the intensity of the laser beam stable even for variations in the supply voltage.

Figure 5:
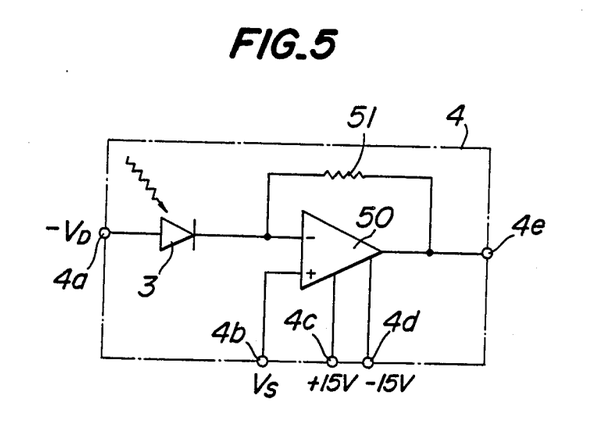
FIG. 5 is a circuit diagram illustrating another embodiment of the light-emitting portion having a temperature compensation circuit.

FIG. 5 is a circuit diagram showing one embodiment of the light-receiving portion 4 in which a circuit is installed for compensating for the effects of temperature, electromagnetic fields and, electrostatic fields applied to the semiconductor photodiode 3. In this embodiment, the anode of the semiconductor photodiode 3 is connected to a bias voltage $-V_D$ through a terminal 4a and the cathode thereof is connected to a negative input terminal of an operational amplifier 50. A feedback resistor 51 is arranged between the negative input terminal and output terminal of the operational amplifier 50. Moreover, the positive input terminal of the operational amplifier 50 is connected to a standard voltage $V_S$ through a terminal 4b. Further, power terminals of the operational amplifier 50 are respectively connected to the power source of $+15$ V and $-15$ V through terminals 4c and 4d. The output terminal of the operational amplifier 50 is connected to a terminal 4e through which a photoelectrically converted output signal is supplied to the external circuits.

In the light-receiving portion 4 mentioned above, since use is made of the operational amplifier 50 having a feedback loop, it is possible to decrease the noise and eliminate the influence of electromagnetic and electrostatic fields. In addition, the operaion thereof can be performed stably even if the temperature is varied, and thus it is possible to effect precise measurements.

Figure 6:
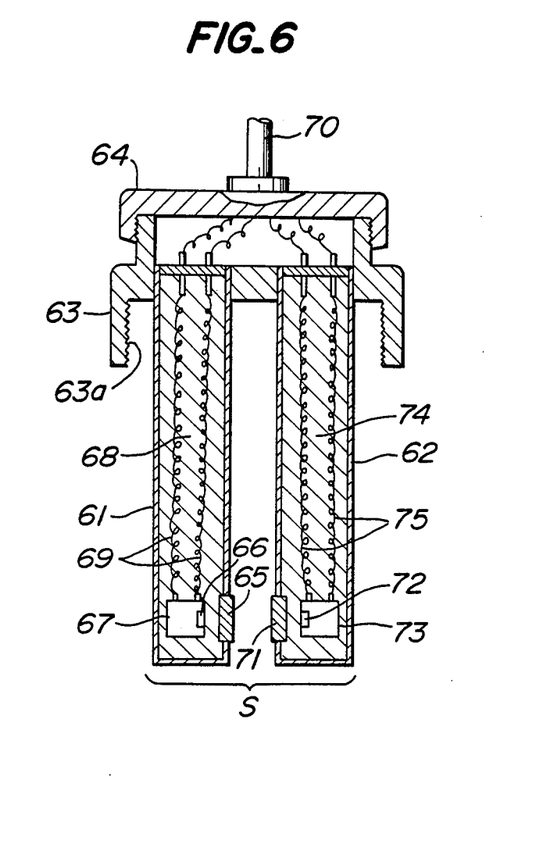
FIG. 6 is a cross sectional view illustrating another embodiment of the turbidimeter according to the invention.

FIG. 6 is a cross sectional view showing another embodiment of the turbidimeter according to the invention. In this embodiment, the housing comprises two cylindrical portions 61 and 62, a support portion 63 for supporting these cylindrical portions on which screw 63a threads are formed for connection with the apparatus containing the test solution to be measured and a cap portion 64 engaged with the support portion 63. At the tip of the cylindrical portion 61 is formed a hole to which a light scattering plate 65 is secured. In addition, a light-emitting portion 67 including a semiconductor laser diode 66 is arranged opposite to the light scattering plate 65. Further, a heat insulating material 68 having a heat insulating and an electrical insulating characteristics is filled in the cylindrical portion 61. The heat insulating material 68 is made of transparent material with respect to the laser beam emitted from the semiconductor laser diode 66. Lead wires 69 connected to the light-emitting portion 67 are extended in the heat insulating material 68, and are connected to the external circuit through a pipe 70. As with the embodiment mentioned above, the other cylindrical portion 62 has a hole in which a light scattering plate 71 is secured. Further, a light-receiving portion 73 including a semiconductor photodiode 72 is arranged opposite to the light scattering plate 71, and a heat insulating material 74 is filled in the cylindrical portion 62. Moreover, lead wires 75 connected to the light-receiving portion 73 are extended in the heat insulating material 74 and are connected to the external circuit through the tubular sleeve 70.

In this embodiment, the semiconductor laser diode 66 and the semiconductor photodiode 72 are thermally insulated by the heat insulating materials 68 and 74, and thus the breakage of these diodes due to the high temperature does not occur. However, if use is made of a semiconductor laser diode 66 and a semiconductor photodiode 72 having relatively low maximum permissive temperatures when current flows therethrough, it is advantageous to use the turbidimeter shown in FIG. 2 because in the embodiment of FIG. 6 the turbidimeter is exposed to an atmosphere having high temperature during sterilization.

As for the semiconductor laser diode used in the tubidimeter according to the invention, use is made of the semiconductor laser diode such as Al—Ga—As, Ga—As—P or In—As—P. Moreover, as for the semiconductor photodiode, use is made of a silicon or a germanium semiconductor diode, but it is especially preferable to use the semiconductor laser diode of the Al—Ga—As in combination with the silicon semiconductor diode. Moreover, as for the semiconductor photodiode, it is preferable to use a PIN photodiode having especially high sensitivity.

Figure 7:
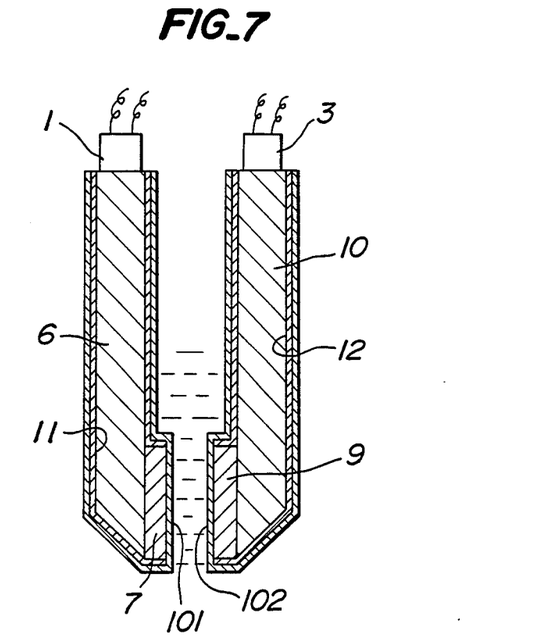
FIG. 7 is a cross sectional view showing still another embodiment of the turbidimeter according to the invention.
Figure 8:
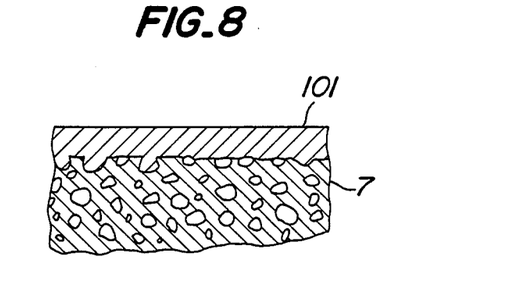
FIG. 8 is a cross sectional view illustrating the surface condition of a light scattering plate.

FIG. 7 is a cross sectional view showing another embodiment of the turbidimeter according to the invention. Portions in FIG. 7 similar to those shown in FIG. 1 are denoted by the same reference numerals used in FIG. 1 and the explanations thereof are omitted here. In this embodiment, as for the light scattering plates 7 and 9, use is made of a translucent or opaque quartz plate containing a number of fine bubbles therein. Such a translucent quartz plate may be obtained by melting a raw material i.e. silica produced in Korea at a temperature between 1,700° and 2,200° C. and then by slowly cooling the melt. The diameter of each bubble is preferably about 10 to 100 μm, and the number of bubbles in 1 mm$^2$ is about 150 to 250. The dimension of the light scattering plate used in the turbidimeter is 2.2 mm by 2.0 mm and the thickness thereof is 1.0 mm. Further, in the present embodiment, a silicon varnish, is applied on the light scattering plates 7, 9 and on the metal mirrors 11, 12 so as to form varnish layers 101 and 102. Instead of silicon varnish, use may be made of glass having a low melting point or Japanese lacquer. Since use is made of the varnish layers 101 and 102 as mentioned above, it is possible to make smooth the surface of the light scattering plate 7 by filling up concave portions formed on the light scattering plate 7 with the varnish layer 101 as shown in FIG. 8. If the varnish layers 101 and 102 are not provided on the light scattering plates 7 and 9, the fine particles etc. in the suspension might intrude into the concave portions. In this case, since the particles intruded in the concave portions are not easily removed therefrom, a measurement error might occur, and thus more precise measurements could not be performed.

The inventors have found that the light scattering plate made of translucent or opaque quartz containing fine bubbles is particularly suitable for scattering the near infrared or infrared rays emitted from the semiconductor laser diode. For instance, the Al—Ga—As laser diode emits near infrared ray having a center wavelength of 780 nm, and a light scattering plate made of translucent or opaque quartz containing small bubbles can scatter this near infrared ray very effectively. The translucent or opaque quartz can be obtained by melting siliceous stones and sands at a temperature within a range of 1,700° to 2,500° C., particularly 1,700° to 2,200° C., and then by gradually cooling the melt. The number of bubbles per unit area may vary depending upon the country in which the siliceous stones and sands are produced. For instance, by suitably combining siliceous stones and sands produced in Korea and India it is possible to manufacture translucent quartz have the desired property. If the number of bubbles is too large, the bubble distribution may be decreased by adding powders of transparent quartz. It has been further confirmed that there is no significant relation between the size of siliceous stones and sands and the size and distribution of bubbles. Further the inventors have confirmed experimentally that it is preferable to use as the raw material siliceous stones and sands, particularly white siliceous stones having high purity. When securing a light scattering plate made of translucent or opaque quartz containing fine bubbles to a light guide made of transparent or clear quartz, a glass layer having a low melting point is applied on a contact surface and then the assembly is heated to a temperature higher than the melting point. In this manner, the light scattering plate can be easily and firmly cemented to the quartz light guide.

The present invention is not limited to the embodiments mentioned above, but various modifications are possible. For example, in the embodiments explained above, the light scattering plate is arranged at the light-emitting portion and the light-receiving portion of the laser beam, but one or both of them may be eliminated. Moreover, in the embodiment shown in FIGS. 1 and 2, use may be made of an optical fiber instead of a prism. Further, in the temperature compensation circuit shown in FIG. 4, it is possible to install a protection circuit for cutting off the current flowing through the semiconductor laser diode 1 when the current becomes extremely large. In this case, it is possible to eliminate the protection circuit including the thermistor shown in FIG. 3. Moreover, in the embodiment shown in FIG. 7, in which silicon varnish is applied on the surface of the light scattering plate to make a smooth surface thereof, use may be made of a lacquer or a glass having a low melting point. Further, it is possible to make the surface smooth by fusing it with heat.

The advantages of the present invention mentioned above are summarized as follows.

(1) Since use is made of a semiconductor laser diode as the light source and a semiconductor photodiode as the light-receiving unit and these diodes are integrally arranged in the detection portion, it is possible to obtain a turbidimeter which is small in size and light in weight.

(2) Since use is made of a semiconductor laser diode, it is possible to obtain a light output having high intensity, so that turbidity can be measured accurately over a wide range.

(3) Since the semiconductor laser diode and the semiconductor photodiode are inexpensive the cost of the whole turbidimeter can be reduced.

(4) Since the influence of temperature upon the semiconductor laser diode and semiconductor photodiode is eliminated, these diodes can not be broken. Therefore, if the turbidimeter according to the invention is utilized in a fermentation apparatus, it is not necessary to remove the turbidimeter from the fermentation apparatus each time the apparatus is sterilized at a high temperature, and thus the operation thereof can be made simple.

(5) Since use is made of a temperature compensating means for the semiconductor laser diode and the semiconductor photodiode, it is possible to effect an accurate and stable measurement even if the temperature is varied.

(6) Since the influence of electromagnetic and electrostatic fields upon the semiconductor photodiode can be reduced, it is possible to effect an accurate measurement even if the turbidimeter according to the invention is utilized in a fermentation apparatus using a magnetic stirrer.

(7) Since the temperature of the region to be measured is detected and then the semiconductor laser diode is forcedly made inactive when the detected temperature rises above a predetermined temperature, the semiconductor laser diode can be advantageously protected from breakage due to the high temperature.

(8) When a light scattering plate made of translucent or opaque quartz having fine bubbles contained therein is used, strong light having a wavelength within a mid range of 180~4,000 nm can be scattered effectively. Further, translucent or opaque quartz can be manufactured easily and can be used stably for a very long time.

What is claimed is:

1. A turbidimeter for measuring the turbidity of a test liquid, comprising
   a hollow housing having a lower end with an aperture, said housing being immersible in said test liquid to permit said test liquid to enter said housing through said aperture;
   a semiconductor laser diode mounted within said housing for emitting a laser light beam, said light beam being incident upon the test liquid within said housing;
   a semiconductor photodiode mounted within said housing for receiving light emanating from said test liquid within said housing, said photodiode generating an electrical signal corresponding to the turbidity of said test liquid; and
   means for compensating for the influence of temperature upon said semiconductor laser diode and said semiconductor photodiode.

2. A turbidimeter according to claim 1, which further comprises a transparent heat insulating member arranged within said housing.

3. A turbidimeter according to claim 2, wherein said semiconductor laser diode and photodiode are arranged within said transparent heat insulating member at the lower end of said housing.

4. A turbidimeter according to claim 2, which further comprises
   first and second light scattering plates, said first light scattering plate being interposed between said laser diode and said test liquid, and said second light scattering plate being interposed between said test liquid and said photodiode.

5. A turbidimeter according to claim 4, wherein said first and second light scattering plates are made of translucent quartz having a number of fine bubbles contained therein.

6. A turbidimeter according to claim 5, wherein the diameters of the fine bubbles in said translucent quartz are in the approximate range of 10 to 100 μm.

7. A turbidimeter according to claim 6, wherein the density of the fine bubbles in said translucent quartz is in the approximate range of 150 to 250/mm$^2$.

8. A turbidimeter according to claim 1, wherein said hollow housing comprises a portion for securing the turbidimeter to a vessel containing said test liquid.

9. A turbidimeter for measuring the turbidity of a test liquid comprising
   a hollow housing having first and second ends with an aperture located at the first end thereof, said housing being immersible in said test liquid to permit said test liquid to enter said housing through said aperture;
   a semiconductor laser diode mounted within said housing at said second end for emitting a laser light beam;
   a first light quide member made of light transmitting and heat insulating material, said first light guide member being arranged within said housing for guiding the laser light beam emitted by said laser diode into the first end of said housing and making said laser light beam incident upon the test liquid within said housing;
   a second light guide member made of light transmitting and heat insulating material, said second light guide member being arranged within said housing for guiding light emanating from the test liquid within said housing into the second end of said housing;
   a semiconductor photodiode arranged within said housing at said second end for receiving the light emanating from said second light guide member, said photodiode producing a signal corresponding to the turbidity of the test liquid; and
   means for compensating for the influence of temperature upon said semiconductor laser diode and said semiconductor photodiode, said means further preventing the flow of current through said semiconductor laser diode and said semiconductor photodiode when said diode and photodiode are subjected to high temperatures such as during sterilization of said turbidimeter.

10. A turbidimeter according to claim 9, wherein each of said first and second light guide members is formed by a quartz prism.

11. A turbidimeter according to claim 9, wherein said first and second light guide members are covered with light reflection layers except for light inlet and exit surface portions thereof.

12. A turbidimeter according to claim 9, wherein said housing further comprises a portion for securing the turbidimeter to a vessel containing said test liquid.

13. A turbidimeter according to claim 12 wherein said means for compensating for the influence of temperature comprises a circuit for protecting said semiconductor laser diode and said semiconductor photodiode, said circuit cutting off the current flowing through at least one of said laser diode and semiconductor photodiode when the environment temperature exceeds a predetermined temperature.

14. A turbidimeter according to claim 13, wherein a potentiometer is provided in said circuit for adjusting said predetermined temperature.

15. A turbidimeter according to claim 12, further comprising means for keeping the light intensity of said semiconductor laser diode constant with variations in temperature.

16. A turbidimeter according to claim 12, further comprising means for compensating the effects of temperature, electromagnetic and electrostatic fields upon said laser diode and photodiode.

17. A turbidimeter for measuring the turbidity of a test liquid, comprising
a hollow housing having first and second ends with an aperture located at the first end thereof, said housing being immersible in said test liquid to permit said test liquid to enter said housing through said aperture;
a semiconductor laser diode mounted within said housing at said second end for emitting a laser light beam;
a first light guide member made of light transmitting and heat insulating material, said first light guide member being arranged within said housing for guiding the laser light beam emitted by said laser diode into the first end of said housing and making said laser light beam incident upon the test liquid within said housing;
a second light guide member made of light transmitting and heat insulating material, said second light guide member being arranged within said housing for guiding light emanating from the test liquid within said housing into the second end of said housing;
a semiconductor photodiode arranged within said housing at said second end for receiving the light emanating from said second light guide member, said photodiode producing a signal corresponding to the turbidity of the test liquid;
a light scattering means arranged between the first light guide member and the second light guide member within the housing the scattering the light beam transmitted therethrough; and
means for compensating for the influence of temperature upon said semiconductor laser diode and said semiconductor photodiode, said means further preventing the flow of current through said semiconductor laser diode and said semiconductor photodiode when said diode and photodiode are subjected to high temperatures such as during sterilization of said turbidimeter.

18. A turbidimeter according to claim 17, wherein said light scattering means comprises
a first light scattering plate interposed between the first light guide member and the test liquid within the housing; and
a second light scattering plate interposed between the test liquid within the housing and the second light guide member.

19. A turbidimeter according to claim 18, wherein said first and second light scattering plates are made of translucent quartz having a number of fine bubbles contained therein.

20. A turbidimeter according to claim 19, wherein the diameters of the fine bubbles in said translucent quartz are in the approximate range of 10 to 100 $\mu$m.

21. A turbidimeter according to claim 20, wherein the density of the fine bubbles in said translucent quartz is in the approximate range of 150 to 250/mm$^2$.

22. A turbidimeter according to claim 19, which further comprises first and second layers applied on surfaces of said first and second light scattering plates, respectively, said surfaces facing the test liquid within said housing.

23. A turbidimeter according to claim 22, wherein said first and second layers are made of a material selected from a group consisting of silicon varnish, lacquer and glass having a low melting point.

24. A turbidimeter according to claim 18, wherein said first and second light scattering plates are made of opal glass.

25. A turbidimeter according to claim 17, wherein said housing comprises a portion for securing the turbidimeter to a vessel containing said test liquid.

26. A turbidimeter according to claim 17, wherein said first and second light guide members are formed by quartz prisms.

27. A turbidimeter according to claim 26, wherein said first and second quartz prisms are covered with light reflecting layers except for light inlet and exit surface portions thereof.

28. A turbidimeter according to claim 27, wherein said semiconductor laser diode is formed by a laser diode selected from the group consisting of Al—Ga—As, Ga—As—P and In—As—P laser diodes.

29. A turbidimeter according to claim 27, wherein said semiconductor photodiode is formed by a photodiode selected from a group consisting of silicon, germanium and PIN photodiodes.

* * * * *